(12) United States Patent
Scruggs

(10) Patent No.: US 11,197,753 B2
(45) Date of Patent: Dec. 14, 2021

(54) PROSTHETIC HEART VALVE CREATING A VORTEX EFFECT

(71) Applicant: James A. Scruggs, Memphis, TN (US)

(72) Inventor: James A. Scruggs, Memphis, TN (US)

( * ) Notice: Subject to any disclaimer, the term of this patent is extended or adjusted under 35 U.S.C. 154(b) by 0 days.

(21) Appl. No.: 15/821,739

(22) Filed: Nov. 22, 2017

(65) Prior Publication Data

US 2020/0405479 A1     Dec. 31, 2020

Related U.S. Application Data

(60) Provisional application No. 62/425,076, filed on Nov. 22, 2016.

(51) Int. Cl.
    *A61F 2/24*          (2006.01)

(52) U.S. Cl.
    CPC ............. *A61F 2/24* (2013.01); *A61F 2/2418* (2013.01); *A61F 2/2427* (2013.01); *A61F 2210/0057* (2013.01); *A61F 2220/0075* (2013.01)

(58) Field of Classification Search
    CPC ........ A61F 2/2418; A61F 2/24; A61F 2/2476; A61F 2/2478; A61F 2/2487; A61F 2002/484; B04C 3/00; B04C 9/00; F15D 1/009; F04F 1/00; F04F 5/00
See application file for complete search history.

(56) References Cited

U.S. PATENT DOCUMENTS

| | | | | | |
|---|---|---|---|---|---|
| 4,019,720 | A | * | 4/1977 | Levesque | B29B 7/32 366/96 |
| 5,554,186 | A | * | 9/1996 | Guo | A61F 2/2403 623/2.28 |
| 9,480,559 | B2 | * | 11/2016 | Vidlund | A61L 27/34 |
| 9,867,697 | B2 | * | 1/2018 | Alkhatib | A61F 2/2418 |
| 10,111,749 | B2 | * | 10/2018 | Sheahan | A61F 2/2412 |

* cited by examiner

*Primary Examiner* — Yashita Sharma
*Assistant Examiner* — Amanda M Barkan
(74) *Attorney, Agent, or Firm* — William S. Parks

(57) ABSTRACT

A prosthetic heart valve either of the mechanical type or the bio prosthetic type, comprises a tubular or cylindrical frame element, a plurality of injectors, a suturing member surrounding the tubular or cylindrical frame element, tether lines to secure the device during diastolic filling but more predominantly during systolic contraction that creates a vortex effect with externally supplied pressurized fluid injected angularly within a transport structure is provided. Such a unit is utilized to accelerate the hemodynamics, reduce the energy required for said transport or both. The annular frame is designed to allow a passageway for blood flow and regulating flow during systolic contraction. Such a result is achieved through the introduction of pressurized fluid (blood) via a plurality of injectors situated evenly around the circumference of the subject tubular or cylindrical unit, and angled uniformly for an even pressure injection of fluid within the conveyance component thereof.

10 Claims, 3 Drawing Sheets

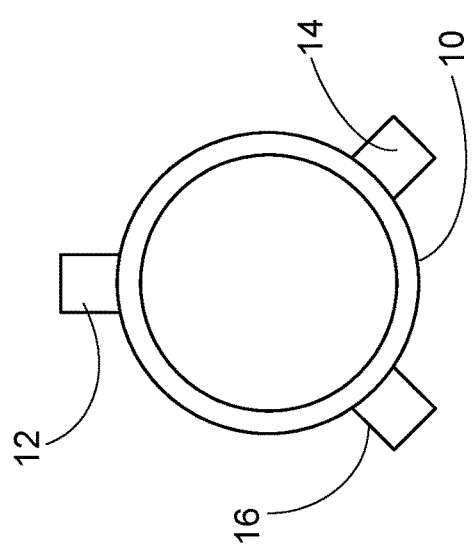
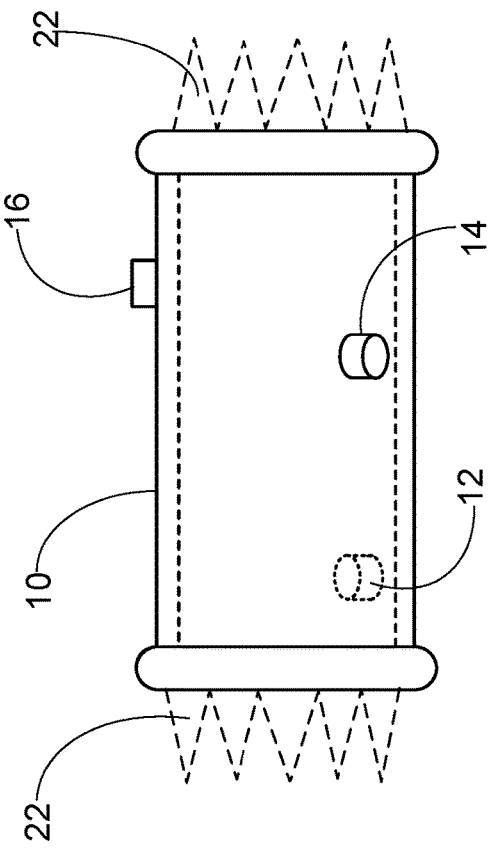
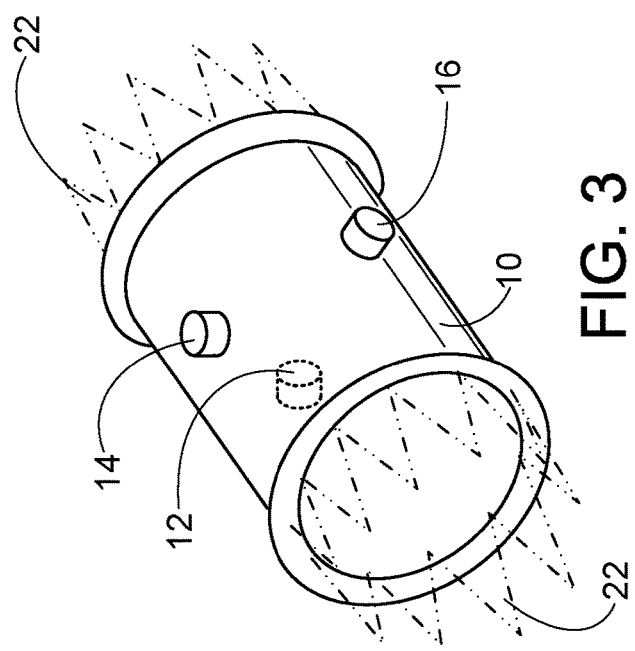
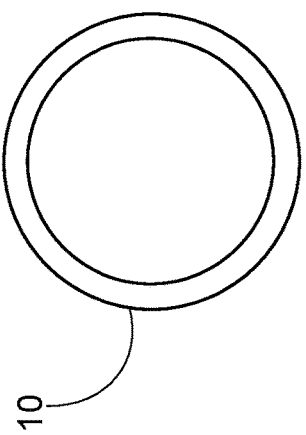

PROSTHETIC HEART VALVE CREATING A VORTEX EFFECT

CROSS-REFERENCE TO RELATED APPLICATION

This application claims priority to U.S. Provisional Patent Application No. 62/425,076, filed on Nov. 22, 2016, the entirety of which is hereby incorporated by reference.

FIELD OF THE INVENTION

A prosthetic heart valve for dynamic utilization within a human or animal heart is provided. Such a valve is a tubular or cylindrical frame element base including a valve element and angularly configured injectors placed around the outer periphery thereof at different locations and distances from the leading or following edge. Such injectors are configured to inject fluid or gas from an external source into the internal portion of such a frame element base to permit control of the valve element with a consistent pressure application for control of the valve element. In such a manner, the external source may act in concert with the heart itself to ensure the valve element is properly and timely controlled at certain pressures to effectuate the desired blood flow results needed not only for healthy activity, but also to an extent that allows for repair and therapeutic results for the user, as well.

BACKGROUND OF THE ART AND INDUSTRY

The present invention is in the field of heart valve prosthesis and implant. More particularly, the present invention is directed to improved chamber hemodynamics. In a large percentage of individuals, one or more heart valves may not function normally. It can be attributed to a disease, degeneration, congenital defect, or trauma force. In the case of the aortic valve, dysfunction can result from stenosis or various forms of valve incompetence. Severe heart valve dysfunction can be life threatening.

Leonardo da Vinci was ahead of his time, in both anatomy and physiology which led to advances in understanding blood flow. Leonardo da Vinci carefully depicted the four chambers of the heart and in addition deduced that eddy currents in the blood flow were created by structures in the main aorta artery. His sketches of the heart valves were extremely detailed. Much has been learned in the following five hundred years.

For close to fifty years, severe heart valve dysfunction has been treated by replacing the valve with a mechanical prosthetic or a bio-prosthetic valve.

A mechanical heart valve typically comprises a ridged circular ring with a flapper valve element constructed of rigid material, for example pyrolytic carbon. The hydrodynamic characteristics of a mechanical heart valve require a patient to be on a carefully monitored dose of anticoagulants. A bio-prosthetic heart valve typically comprises a semi-rigid plastic stent that supports a tissue valve. Commonly used are xenograft and homograft style bio-prosthetic heart valves, such as a porcine aortic valve. Patients receiving bio-prosthetic heart valve implants need not take anti-coagulant drugs. Xenografts are typically treated with glutaraldehyde to minimize antigenic reactions in patients and to aid in preserving the tissue.

Both the mechanical heart valve and the bio-prosthetic heart valves have suture rings of various designs to allow the surgeon to precisely anchor the valve in position, for example, the aortic annulus. Typically, the suturing ring comprises a circular fashion fabric structure surrounding the metal seat of the mechanical heart valve or the fabric covered stent of the bio-prosthetic heart valve.

The majority of the technological advancement in heart valves whether mechanical or bio-prosthetic in nature has been to improve the hemodynamics of the patient by replacing the dysfunctional native valve. Other advancements have come in the way the valves are attached to the annulus, rotatable cuffs and methods of keeping the installed valves in the proper relative axis.

The present development creates the possibility of a new field of prosthetic mechanical heart valves and bio-prosthetic heart valves that can be implanted in the heart chambers whose purpose is not to replace the native valve, but instead improve the overall performance of the chamber. For example, a device that could help the left ventricle more easily overcomes the resistance of afterload. This permits installation of a chamber implant device of either variety in patients that have all native hearts as well as patients that have one or more artificial replacement valves.

Blood flow is accomplished through certain valves such as the tricuspid, pulmonary, mitral, and aortic that is known to create a natural vortex effect that spins off negative charges. These valves are passageways that regulate when and where blood is transported. A healthy human heart pumps approximately 2000 gallons of blood through its chambers a day. Patients with heart disease often experience reduced flow from their heart chambers diminishing their overall health.

From hemodynamics, we know the heart is the driver of the circulatory system, pumping blood through rhythmic contraction and relaxation creating cardiac output. The current artificial heart replacement valves, such as mechanical, prosthetic, tissue, or bio prosthetic types, do not provide similar effects, thus limiting the effectiveness of such synthetic structures. For instance, if such an artificial valve could spin off negative charges in the left ventricle and efficiently increase the laminar blood flow, optimal blood transport results could be realized.

Unfortunately, such is not the case, and the standard artificial valves cannot efficiently treat cardiomyopathy. There are devices that are implantable that electrically stimulate the chamber wall of the ventricle to relieve wall stress. There are other conditions that lead to inefficient blood flow into and out of chambers that are not directly attributable to dysfunctional valves. This could as well relate to hypotension (low blood pressure).

In addition, standard heart replacement valves have many meritorious medical benefits when the native valve is dysfunctional; however, they do little to aid overall chamber cardiac output when chamber output is deteriorated due to a weak or diseased chamber.

Ventricular assist devices (VADs) are cumbersome at least and can limit the patient's mobility and usually require an external pump or air supply. The LVAD (Left Ventricle Assist Device) is the most popular and common, some VADs are implantable and some are transcutaneous. VADs have their place especially in end stage heart failure and they have tremendous benefit during and after surgery, but they still require a pump. The present inventive device can be properly sized and configured to utilize blood as the injected fluid and could be utilized as a more efficient artificial human heart replacement valve that more closely simulates the actual human circulatory system.

This inventive device would appear to pump itself without any moving parts. The truth however, on closer inspection is the transformation of energy occurring as the kinetic energy from the blood entering the chamber and filling the said valve through the open ports of the fluid injectors and striking the transport chamber cylinder wall thereby, causing a rotational motion that starts to create a vortex effect on the transport column. As the dynamic pressure changes the fluid exits the transport column and thereby creates a negative pressure on the opposite side of the transport column, thereby creating a pulling force to attract more blood into the transport column. Now as the dynamic pressure starts to rise during systole contraction the blood flow would naturally increase within the transport chamber as the laminar column of blood exits the transport column in the optimal direction in this case towards the aortic valve until the pressure in the chamber reaches the value desired to open the aortic valve. The difference is that when it does open the chamber is assisted by the hemodynamics of this said device and thereby, more blood leaves the chambers with less energy to produce this flow.

In comparison with standard artificial heart valves, the inventive device could also reduce clotting and other undesirable factors, as well. It is important to note that this inventive device can be used in conjunction with patients that have artificial heart valves implants as well as patients that do not have artificial valve implants. The current mechanical, prosthetic and or bio prosthetic heart valves accomplish many meritorious benefits to patients, however they do not significantly improve the mean velocity and thus Reynold's number translating to optimal blood flow into and out of the heart chambers in the same manner. This number is received by comparing inertial force with viscous force.

Reynolds Number=Inertial Force
Viscous Force $$NR = pvL/\mu$$

p=density of the blood
v=mean velocity of the blood
L=characteristic dimension of the vessel in this case diameter
µ=viscosity of blood Basically, a Reynolds Number of less than 2300 is laminar flow, whereas a value over 4000 is represented as turbulent flow. Thus, one significant advantage of the present invention is the ability to reduce dynamic pressures and improved hemodynamics within a circulatory tube/pipe or vessel with energy levels far lower than a typical circulatory system without this device. Yet, another advantage is the inventive system is to reduce ineffective and deleterious turbulence within the circulatory system. A final advantage of the inventive device is that because it produces a vortical flow it can also spin off negative charges due to the magnetic field a vortical flow produces similar to the normal vortical flow a healthy human heart produces naturally. (Note: The term vortical in this reference does not correlate to turbulent. The actual improved flow is laminar or in extreme cases transient flow.)

Another problem with cardiomyopathy, whether dilated or hydrotropic, is how it affects the heart muscle and the way it pumps blood from the left ventricle to the rest of the human body. The disclosed device will aid a weak, dilated, or hydrotropic cardiomyopathy heart pump blood more efficiently like a normal healthy heart. The field of hemodynamics would be benefitted by my inventive vortex effects valve as a valuable alternative to heart transplant surgery, various ventricle assist device (VLAD) or merely relying on pharmaceuticals, blood thinners and merely drugs to improve blood flow. A healthy heart expels approximately fifty five percent of the blood in the chambers, but patients with heart disease have substantially reduced percentage chamber output.

The inventive device can be sized and modified to improve the hemodynamics, affecting the pressure/flow relationship and the laminar flow into and out of the various heart chambers and thus improve the circulatory system of the patient. Thereby, the inventive device aids the circulatory system in transporting more oxygen in a patient's cardiovascular system. The Reynolds number is utilized to check whether the flow is laminar or turbulent. This number is received by comparing inertial force with viscous force.

$$Re = pVL/\mu$$

First, from fluid dynamics we know the following equation:
Dynamic pressure=q
q=½pv2
q=dynamic pressure
p=fluid density
v=velocity
µ=viscosity of the fluid
Measured in Pascals We know that dynamic pressure is the kinetic energy per unit volume of a fluid particle. We also know that dynamic pressure is equal to the difference between the stagnation pressure and the static pressure.

There is thus a need to provide an effective change in such dynamic pressure measurements in the human heart in order to provide greater efficiencies. Thus, the energy from the human blood passing thru orifices (injectors) in the sidewall of the vortex effects bio prosthetic vortex valve would angularly strike the interior sidewall of the valve and create the vortex effect.

Blood is characteristic of a Non-Newtonian fluid while plasma is more closely characteristic of a Newtonian fluid being comprised primarily of water, proteins and saline. This allows one to take into account shear stress (or deformation force) on blood cells. One could look at Bernoulli's principal that the speed of a fluid occurs simultaneous with a decrease in pressure or a decrease in the fluid's potential energy, which in some situation will help describe the flow through an orifice, however the flow stream is not subjected to extreme angular momentum as occurs as the fluid strikes a cylinder wall. Euler equation behavior of non-Newtonian fluids and Navier-Stokes Equations and all other continuum equations have their relevance, the Cauchy equation is best at describing convective acceleration. Convective acceleration can best be described as the effect of time independent acceleration of a flow is a spatial effect, such as fluid speeding up in a nozzle, thus providing a clearer understanding describing the behavior occurring. In this case convection takes place through advection, diffusion and in a new form vortex effect (ve) frictional coefficient reduction.

Furthermore, from the theorem of the conservation of energy; that energy is not constant and neither created or destroyed, just changed in form.

To that end, then, the energy from the blood angularly striking the wall of the cylinder wall changes the dynamic pressure of the vacuum column and thus apparently providing an explanation as to why the vacuum column seems to require less energy to move material and liquid into and out of the heart.

The invention described herein uses blood contacting the tubular wall to change the dynamic pressure of the valve. This creates the vortex effect and aids the weakened heart simulate a healthy heart and actual human circulatory system, a device and overall system/method that has heretofore not been provided, particularly through a dynamic platform.

DETAILED DESCRIPTION OF THE INVENTION

As stated above, blood flow into and out of the heart is accomplished through certain valves that are known to create a natural vortex effect that spins off negative charges. The current artificial heart replacement valves do not provide similar effects, thus limiting the effectiveness of such synthetic structures. For instance, if such an artificial valve could spin off negative charges in the left ventricle, optimal blood transport results could be realized. Moving blood efficiently through the circulatory system requires a lot of energy from the human heart due to the effects of gravity, the speed of conveyance and the proper timing of sequence of the existing heart valves. The current heart valves open and close regulating flow, however they do not help a damaged or weak heart increase flow, nor do they increase the dynamic pressure. My inventive device would be surgically implanted into the patients' left ventricle, and or right ventricle, and enhance the patient's cardiac output. Space allowing the inventive device could be placed in any of the four heart chambers including the two atria and the two ventricles. The inventive device can be sized based on location and hemodynamics desired.

As we know by the equation v=Q/A, where v=velocity (cm/s), Q=blood flow (ml/s), and A=cross sectional area (cm 2), the inventive device would aid the efficiency of the heart chamber to transport blood out of the chamber while improving the laminar flow. As blood enters the chamber it would flow past and through the inventive device and upon contraction the pressurized fluid would enter the orifices and or orifices angular tubes and the pressure stream would angularly strike the cylinder wall changing the dynamic pressure of the stream which in turn would change the atmospheric pressure inside the tubular cylinder, this vortex effect changes the differential pressure such that the energy from the blood can be utilized to change the dynamic pressure of the outgoing blood flow stream. The increased laminar flow would be realized. The inventive device reduces the frictional drag and effective weight of liquids, solids and granular material being through a blood transport column.

The claimed inventive device differs from what currently exists. Existing units in the field are fairly effective when the native valve is dysfunctional such as stenosis, and regurgitation. The timing of the valve's opening and closes is another consideration.

The present invention utilizes the kinetic energy of the blood traveling thru fluid injector ports and striking the interior sidewall of the transport structure tube creating a vortex effect. This vortex effect begins during diastolic filing of the chamber, as blood flows into the transport device and more predominantly during systolic contraction. Dynamic pressures through such devices are measurable, at least in terms of fluid dynamics, by the equation:

$$q = \tfrac{1}{2}p * v2$$

where q is dynamic pressure measured in Pascals, p is fluid density, and v is velocity through the device. Such dynamic pressure is equal to the difference between stagnation pressure and static pressure. There is thus a need to provide an effective change in such dynamic pressure measurements within a circulatory system. To that end, as is stated in the conservation of energy theorem: energy is constant and is neither created or destroyed, just changed in terms of form. Thus, the kinetic energy of the blood exhibits a pressure stream that angularly strikes the tubular and/or cylinder transport structure wall and modifies the hemodynamic pressure of the transport device during systolic contraction. Such changes evince reductions in energy to move materials in such devices as a result. The current artificial heart replacement valves do not provide similar results. The inventive valve is directional thereby, can be utilized to either accelerate or inversely decelerate the transport column. Therefore, the inventive device can be tethered to the chamber wall in the direction to achieve the optimal result due to the varied irregular shape of various patients' heart chambers. Many of the artificial heart valves prosthesis are very successful in native valve replacement and possess very meritorious benefits, but this inventive device is unique in that it can be implanted in patients with native valves, and/or a mixture of native and prosthetic heart valves and in either case improve the hemodynamics of the chamber. An example would be a patient with cardiomyopathy whether dilated or hydrotropic affects the heart muscle and the way it pumps blood from the left ventricle thru the aortic valve to the rest of the human body. The inventive device will aid a weak, dilated, or hydrotropic cardiomyopathy heart pump blood more efficiently like a normal healthy heart. The improved hemodynamics both in the form of increased cardiac output or as adjusted by weight and more commonly utilized improved cardiac index. In the case of mechanical and or bio-prosthetic valves such as (synthetic heart valves, for instance) all suffer from the same associated limitations, although some transport gains can be achieved through such devices may be accomplished to a certain degree, their effectiveness has proven compromised when coupled to the necessary energy generation needed for operation and/or the valves themselves lack the effective transport result at the rate and in the same manner as is necessary for proper actions within the selected milieu.

Yet another advantage of the inventive valve is the ability to reduce ineffective and deleterious flow turbulence in the transport device and the flow stream to the directed valve whether it is native or prosthetic. The increased laminar flow more closely resembles the actions of a healthy heart chamber with a healthy native valve. The improved hemodynamics reduces the nidus of thrombus formation.

During systolic contraction not all of the blood leaves the chamber, a typical percentage in an average healthy ventricle is approximately fifty five percent. For various reasons when the percentage decreases significantly over a prolonged period of time and thousands of cycles the actual chamber walls can become stressed, diluted and the overall patient health can deteriorate. The reduced chamber cardiac index can lead to increased potential thrombosis and sometimes associative Differences in mean blood pressure are responsible for blood flow from one location to another in the circulation system.

Durability is definitely a crucial factor in the clinical applicability of any heart valve as existing heart replacement valves must open and close approximately four million times a year. The inventive device does not open or close, yet it improves the hemodynamics of the heart chamber and reduces chamber wall stress caused from myopathy and reduces thrombosis.

It is thereby also imperative that the material chosen for the valve construction be both immune from biochemical degradation and mechanical failure caused from wear and fatigue of rubbing and flexing and material breakdown.

Pyrolite carbon coating on clean smooth surfaces has excellent inherent qualities to resist thrombosis and is relatively inert towards blood plasma, plasma proteins and plasma enzymes. Pyrolite coatings or skins can be applied to a variety of substrates including metals. The inventive device shall have a Pyrolite coating for main unit and substrates to enhance performance.

Vortex Effect—Note: The inventive device is said to create a vortex effect and in this example and application the device creates an effective outflow that resembles many of the physical properties of a flow, similar to what Osborne Reynolds would have predicted where Laminar Re<2300
Transient 2300<Re<4000+VE (Vortex Effect)
Turbulent when 4000<Re The inventive device as described here, for example, would produce Reynolds Numbers that would be fairly consistently expected and thus the mathematical laws relating to dynamic and kinematic viscosity as they relate to Newton's Law of Friction to a large extent would hold true.

The VE (Vortex Effect) is a force that reduces the frictional drag on a dynamic fluid column and or vacuum column in a pronounced way. This VE force temporarily reduces the effective specific gravity of the fluid column similar to an inverse vortex force. The force is greatest on the outside and less as one approaches the center. Thereby, the frictional coefficient force (drag) the dynamic blood column would exert on the cylinder wall is reduced, allowing the column to increase velocity. This defined velocity changed would be variable based on the inflection angle of the fluid injector in relation to the cylinder wall.

The average stroke volume is approximately 70 ml and the average normal ejection fraction is 55% for normal healthy hearts, but for patients with hearts that afflicted with disease, degeneration, congenital defect or trauma force in which the chamber flow is less than optimal, the patient could benefit from this inventive device.

Accordingly, it is one advantage of the present invention that it provides an improved prosthetic heart valve that can improve cardiac output and thereby either reduce the resistance of afterload (the resistance the left ventricle encounters as it tries to eject blood into the aorta when the chamber contracts), thereby increasing stroke volume. It is another advantage of the present intention to improve the laminar flow from the chamber to the valve whether it is either a native or artificial heart valve. It is still another advantage of the present invention to reduce chamber wall stress by improving the dynamic pressure making it easier for the chamber to function to produce improved cardiac output. The improvement in dynamic pressure in the chamber affects the differential pressure reducing stagnation and prevents incipient thrombosis. The inventive device does not have an opening and closing disc or valve, therefore less items to wear out. It is yet another advantage of the inventive device is the ability to reduce ineffective and deleterious flow turbulence in the heart chamber. The increased laminar flow more closely resembles the flow of a healthier heart chamber reducing the nidus of thrombus formation.

A truly unique feature is adaptability and versatility. The unit can be attached to an existing valve whether native or artificial, the prosthesis heart valve can be attached free-float as in the left ventricle in-line with the aortic valve, or interior the mitral valve chamber and sutured to either a native or artificial mitral valve to aid the filling of the left ventricle. The valve is extremely versatile in that it can be utilized to more efficiently either fill or empty a chamber. It could be utilized in a variety of chambers and sized accordingly. The unit can have a flange to attach to an existing valve or flange-less as in its free-float design with tether lines to maintain axial preference. The inventive device can be constructed as either a mechanical prosthetic heart valve or as a bio-prosthetic valve. Finally, as chamber hemodynamics improves and wall stress reduces, the patient's overall health should improve.

Accordingly, this invention encompasses a prosthetic heart valve either of the mechanical type or the bio prosthetic type, comprising a tubular or cylindrical frame element, a plurality of injectors, a suturing member surrounding the tubular or cylindrical frame element, tether lines to secure the device during diastolic filling but more predominantly during systolic contraction that creates a vortex effect with externally supplied pressurized fluid injected angularly within a transport structure is provided. Such a unit is utilized to accelerate the hemodynamics, reduce the energy required for said transport or both. The annular frame is designed to allow a passageway for blood flow and regulating flow during systolic contraction.

Such a result is achieved through the introduction of pressurized fluid (blood) via a plurality of injectors situated evenly around the circumference of the subject tubular or cylindrical unit, and angled uniformly for an even pressure injection of fluid within the conveyance component thereof. The suturing member surrounds the circular frame element and has a first radial width in a first circumferential region substantially greater than a second circumferential region to define an extended portion of the suturing member Operation:

This inventive device would appear to pump itself without any moving parts. The truth however, on closer inspection is the transformation of energy occurring as the kinetic energy from the blood entering the chamber and filling the said valve through the open ports of the fluid injectors and striking the transport chamber cylinder wall thereby, causing a rotational motion that starts to create a vortex effect on the transport column. As the dynamic pressure changes the fluid exits the transport column and thereby creates a negative pressure on the opposite side of the transport column, thereby creating a pulling force to attract more blood into the transport column. Now as the dynamic pressure starts to rise during systole contraction the blood flow would naturally increase within the transport chamber as the laminar column of blood exits the transport column in the optimal direction in this case towards the aortic valve until the pressure in the chamber reaches the value desired to open the aortic valve. The difference is that when it does open the chamber is assisted by the hemodynamics of this said device and thereby, more blood leaves the chambers with less energy to produce this flow.

As other concerns and possible alternatives, it is noted that the tether sewing ring shall be constructed of biocompatible material such as a polyester fabric, silicones, polyurethanes, and polytetrafluoroethylene (PTFE) to form a fabric ring. An inner biocompatible metal ring constructed of titanium alloy could serve as a cuff retaining ring. The material could be woven or knitted, but in other embodiments may be woven or non-woven structure, wherein, forms a suture sewing ring.

Yet another embodiment, then, includes a valve wherein the cuff portion of fabric tube could be heated above a transition temperature under a compressive load to reduce the thickness of the annular cuff to a generally uniform shape to aid in creating a more even torque range. This could also include a coating or impregnation thru ion-beam substance implantation of materials such as silver, which is toxic to bacteria and/or other microbes.

In another possible embodiment, the length of the transport cylinder and/or the fluid injectors can be varied to change the flow characteristics, as well as the circumferential rims are sharp or rolled with varying approach edges to reduce frictional coefficients. In another embodiment the fluid injectors have an elliptical orifice opening to affect frictional coefficients. In another potential embodiment, the leading edge diameter of the fluid injectors is approximately equal to the orifice size of the injector nozzle to reduce frictional loss because flow through an orifice is proportional to diameter, but for sharp edged orifices the actual flow can be reduced by as much as 65 percent of the theoretical. Efficiency does matter, therefore the transport cylinder diameter and the fluid injectors' diameter will be precise bore through best practices to further enhance performance.

In essence, the overall inventive heart valve fluid transport device is one that allows for more efficient materials transport through the utilization of a plurality of injectors introducing similar and simultaneously introduced fluids within the internal portion of the conveyance component thereof. In this manner, the term fluids is intended to include without limitation, a liquid a gas, or mixtures and/or combinations of multiple liquids, multiple gases, or both gases and liquids. Such a result is achieved thru the introduction of pressurized fluids via a plurality of injectors situated evenly around the circumference of the subject tube, pipe, and/or cylinders, and angled uniformly (at any angle that aims into the internal portion of the conveyance component of the device; a range from 1 to 175 degrees, with from 70 to 145 degrees more preferred, and from 75 to 90 degrees most preferred. For an even injection of fluid within the conveyance component thereof.

In another embodiment, the inventive device is much larger and is utilized in power generation systems. The transport cylinder could range from 3 to 72 inches in diameter and the injection of such fluids at specified angles and at selected pressures and/or velocities allows for the internal generation of a vortex effect within the conveyance component which. In turn, this effect increases the speed of material transport, reduces turbulence (and thus dynamic pressures) within the device, and, overall, allows for energy reductions in terms of assisting air or liquid conveyance or vacuum device utilization for such transport purposes the overall device. Whether horizontally or vertically aligned, and whether such a line includes both vertical and horizontal configurations to allow transport from one location to another, the inclusion of such a plurality of injectors for such a purpose has proven effective for such improved transport results. In the production of electricity generation water is involved in many points in the process. Hydroelectric power converting the energy in falling water into electricity by passing it through turbines. Thereby, the inventive device could reduce the frictional drag on the water column thereby, increasing its velocity as the kinetic energy from the fluid injectors angularly strike the cylinder wall and create a vortex effect on the transport column. Such a result modifies the atmospheric pressure inside the tubular cylinder, thus allowing the vortex effect to modify the differential pressure. In typical hydroelectric power generation, the inventive device could be utilized to improve the water efficiency of the penstock to turn and power the turbine more efficiently. This is accomplished by the transformation of the kinetic energy of the fluid injection aids the potential energy from the dammed water driving the water turbine. The differential pressure causing the vortex effect affects the frictional drag coefficients in the large penstock thereby increasing the velocity of the water column turning the water turbine and thereby generator. This can also aid pumped-storage hydroelectric power stations that have a need to supply energy during high peak demand by pumping water between reservoirs at different elevations. By reducing the energy required by pumped-storage systems will create cost savings. These units can also be utilized in energy reduction savings in wastewater aerators. The power requirements at large wastewater treatment plant can be substantial as many are powered by 4160 volts of electricity. The aerators at these plants typically have large multiple 300 HP centrifugal blowers and/or large positive displacement blowers of larger HP series to provide massive air flow some with some energy savings available by throttling the inlet valve or in the case of the blowers butterfly valves for flow control and surge and vibration protection. This inventive device can be added in-line to reduce the frictional resistance of the air column and thereby, reduce the initial input torque to start the blower to a significant amount and also reduce the running torque, thereby significantly reducing the energy costs of running aerators and bubble diffusers. This can significantly affect the energy efficiency of wastewater treatment plants, which can attribute eighty percent cost of a treatment plant. The secondary treatment achieved in aeration blow air to the biological organisms which feed on the food material present in the wastewater. The organisms form floc, which settle in the circular final settling tanks and then returned to the aeration tanks to maintain higher concentration of organisms to breakdown and thereby treat wastewater.

In still another embodiment, the inventive device can be used to aid research in electron and neutron acceleration. In induced nuclear fission reaction, a uranium-235 nucleus is bombarded by neutrons to turn it briefly into an excited uranium 236 nucleus from the kinetic energy of the neutron as well as the forces that bind the neutron as found in the s and p orbitals. The uranium-236 then splits into faster moving particles and releases three free neutrons, thus creating excitation energy. In a fission application, this inventive device could be constructed on a smaller scale to a vacuum chamber and a free neutron would be accelerated by a laser and a gas (most likely xenon) can be pressurized and sent through a heat resistant alloy gas manifold to the fluid nozzle ports. Such that, the uranium-235 nucleus passes thru the cylinder transport structure and the neutrons are introduced through the fluid injectors and further accelerated by a laser(thermal energy) and increased kinetic energy created by the angular momentum as the neutrons angularly strike the cylinder wall creating a vortex effect and increasing the chain reaction and the energy created as the neutrons strike the uranium-235 nucleus and transforming it into a more powerful more excited uranium-236 nucleus and thereby, setting off a more powerful chain reaction resulting in even more nuclear energy production. This exothermic reaction releases large amounts of energy, electromagnetic radiation and kinetic energy. The inventive device does not create nuclear fission; it just improves its efficiency and improves its energy creation in magnitude. This embodiment utilizes radioactive isotopes and increases the kinetic and excitable energy during fission which can lead to significant increases in the chain reaction and the nuclear excitation as the attraction nuclear force between the neutron and the nucleus occurs at a faster rate with greater kinetic energy causing the isotope atom to split faster and with greater force thereby, further increasing the chain reaction speed and magnitude. Another advantage is that the dynamic pressure inside the nuclear reactor core would allow the nuclear fuel greater utilization as it recirculates through the inventive device and allows more opportunities for the nucleus of the uranium 235 to be pierced by the additional neutrons as the fuel continuously enters and exits the valve and fluid nozzles. The uranium 238 that was thought not to be fissionable would just recirculate with no detrimental effect. It is noted that Uranium 238 when bombarded with neutrons to form Plutonium 239, which is a common occurrence in a nuclear reactor.

These units would work whether the unit is low water (normal water) or heavy water units as utilized predominately in Canada. In this application, the unit is a free-float design constructed of tungsten-carbide, industrial sapphire, or a host of heat resistant alloys material to deal with working temperatures exceeding 2000 degrees Fahrenheit. The unit would be floated in the nuclear fuel into the nuclear core and the unit and or units would float into the nuclear core and would power themselves off the dynamic pressure working on premise of the differential pressure. Therefore, this would create an incredible cost reduction causing more chain reactions in nuclear fuels. The problem with fuel in nuclear reactor cores is that the neutrons introduced need to contact the uranium 235 or radioactive isotopes at the nucleus and there are several components that make up that fuel as well as moderators. This allows slow moving neutrons more opportunities for fission to occur. This also works for other fissionable isotopes. This would also be beneficial for fast neutron bombardment systems such as liquid metal fast breeder reactors.

Another possible embodiment in which the inventive device can be utilized in missile, projectile and warhead applications. The device can utilize in ballistics to reduce the frictional force thereby enhancing thrust. The device can be gas or liquid fuel powered in warheads to increase impact and penetration.

In another potential embodiment the inventive device can be attached to a stent to improve the blood flow in vascular applications and between the kidney and bladder to improve the flow of urine between. The stent utilized can be of various types such as; but, not limited to a coronary, a drug-eluting, a bio absorbable, a bioengineered or a combination thereof. The inventive device can be utilized in conjunction or separately with a prostatic stent. In this application the inventive device is placed from the bladder to allow improve drainage of the bladder through the penis. This would aid in treatment of enlarged prostate. The inventive device can also be utilized to aid bile drainage from the gallbladder, pancreas and bile ducts to the duodenum, but shall be sized accordingly. This would aid in reducing the effects of ascending cholangitis. In the prostatic application the inventive device can be useful in aiding both urination and sexual performance. This utilized in conjunction with a healthy low-fat and high-fiber diet can lead to a healthier prostate.

The features of the present invention can best be understood, together with objects and advantages by reference to the following taken together with the appended, non-limiting drawings.

BRIEF DESCRIPTION OF THE DRAWINGS

FIG. 1 is a top view showing the preferred embodiment of the mechanical heart valve prosthesis of the present invention;

FIG. 2 shows a front view of the same mechanical heart valve prosthesis of FIG. 1;

FIG. 3 shows a top perspective view of the same mechanical heart valve prosthesis of FIG. 1;

FIG. 4 shows a front cross-sectional view of the conveyance component of the same heart valve prosthesis of FIG. 1 (all showing an inventive chamber mechanical prosthetic heart valve that can be attached to a native valve, artificial heart valve, or be of a free-float tethered design in the actual heart chamber);

DETAILED DESCRIPTION OF THE DRAWINGS AND PREFERRED EMBODIMENTS OF THE INVENTION

Without any intention of limiting the breadth and scope of the overall inventive method the following descriptions of the accompanying drawings provide a number of potentially preferred embodiments of the inventive transport improvement device, hence a prosthetic heart valve with vortex effect mechanical and/or bio-prosthetic in nature.

Figure 8:
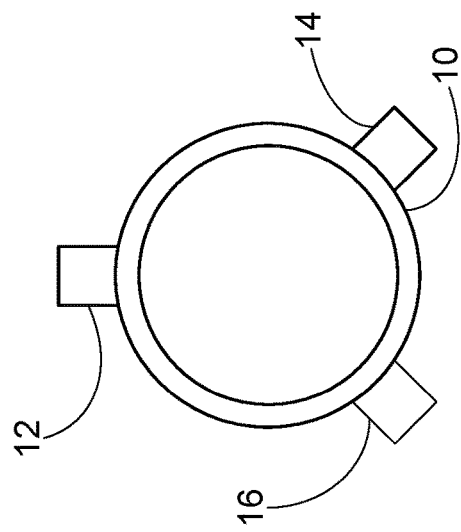
FIG. 8 shows a front cross-sectional view of the conveyance component of the same heart valve prosthesis in FIG. 5.
Figure 5:
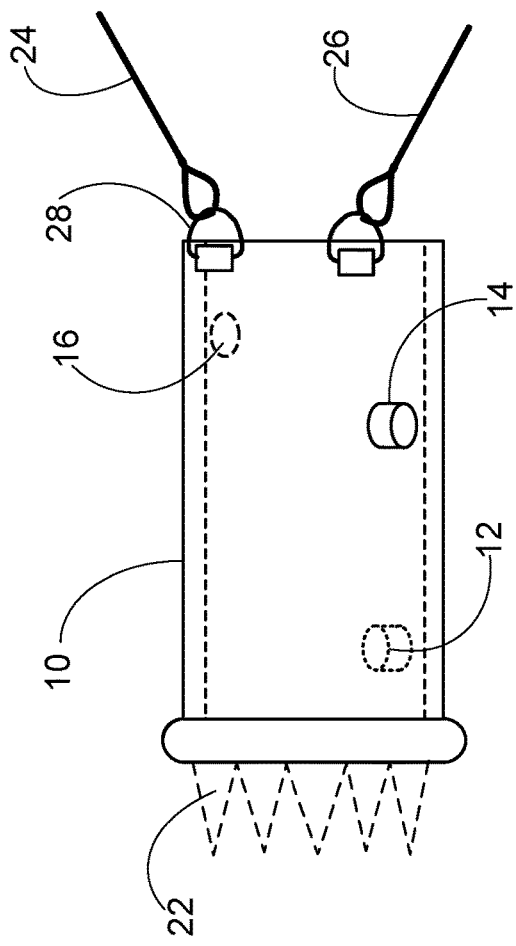
FIG. 5 is a top view showing the preferred embodiment of the chamber mechanical prosthetic heart valve that can be attached to a native valve, artificial heart valve, or by free-float tethered design.
Figure 7:
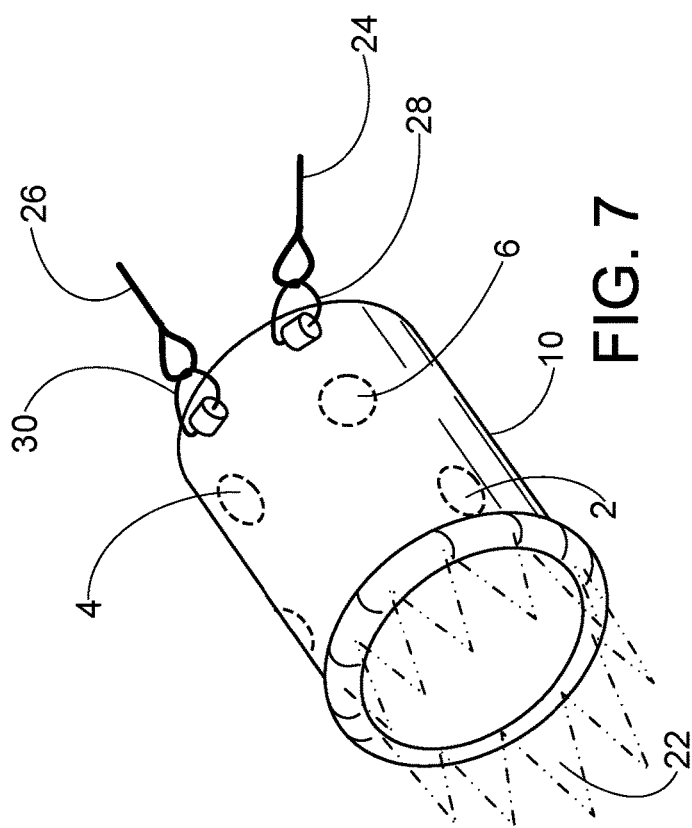
FIG. 7 shows a top perspective view of the same mechanical heart valve prosthesis of FIG. 5.
Figure 6:
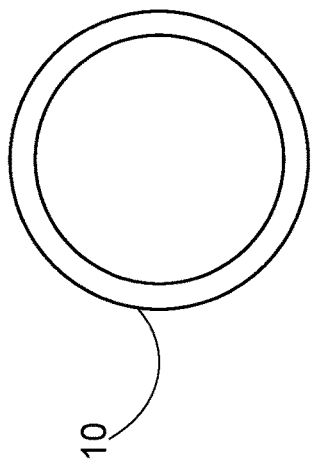
FIG. 6 is a front view of the same mechanical heart valve prosthesis of FIG. 5.
Figure 12:
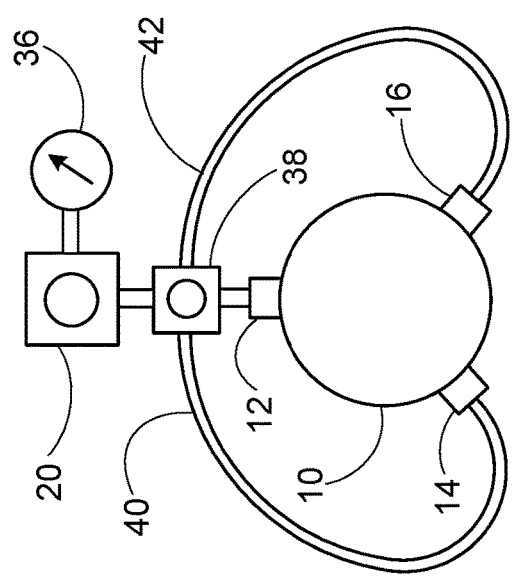
Figure 9:
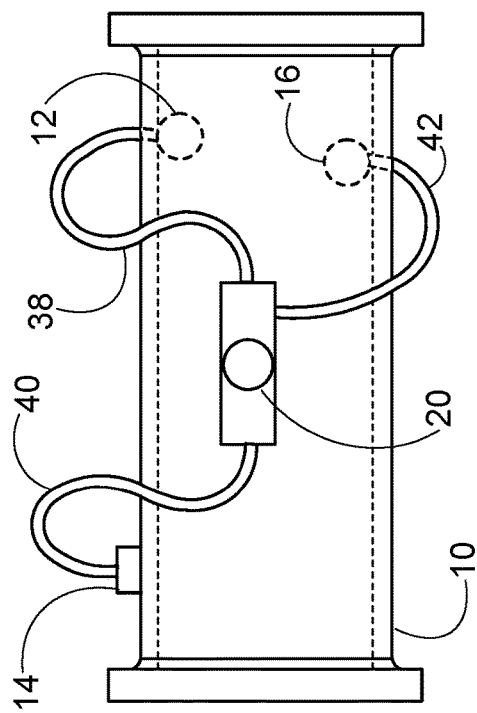
Figure 11:
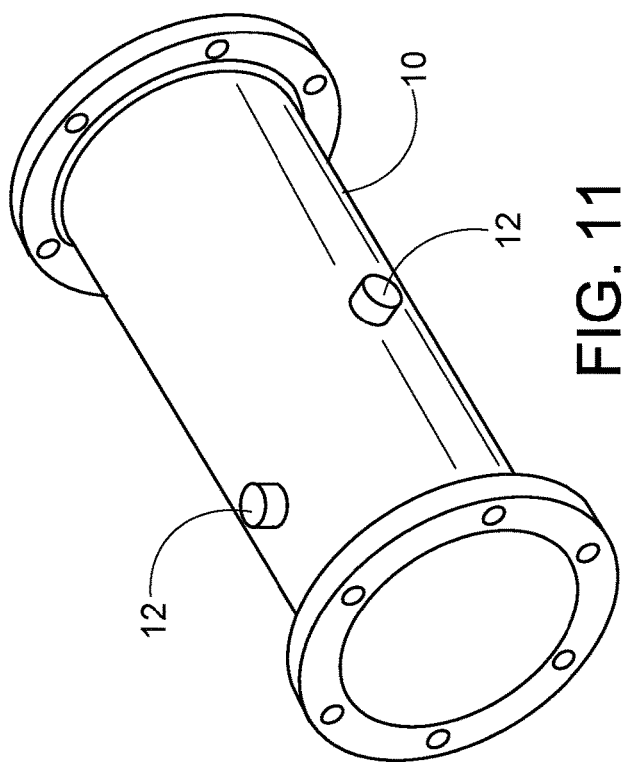
Figure 10:
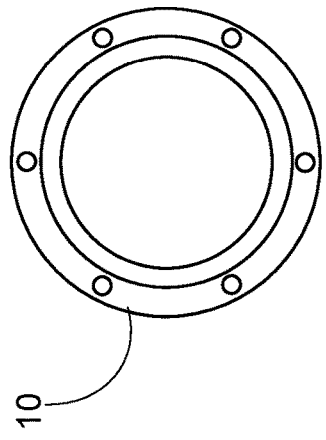

The accompanying Figures provided herein all pertain to different versions of prosthetic heart valves with vortex effect that may be utilized in conjunction with the broadly defined inventive prosthetic heart valve with vortex effect. This prosthesis is usually known in the art as "mechanical" heart valve prosthesis. For specific examples and detailed descriptions of the prior art, reference is made to U.S. Pat. Nos. 3,744,066, 3,835,475, 3,997,923, 4,364,126, and 4,106,129 (structures which are not the same as now described and claimed herein). As noted above and herein, the basic structure is a tubular or cylindrical frame element base 10 to which a plurality of injectors 12, 14, 16 have been incorporated within the conveyance component from an external source and introduced for injection within the internal portion at uniform angles and spaced around the circumference of base cylinder 10. As well, the injectors 12, 14, 16 are preferably connected simultaneously to the same fluid source (20 in FIGS. 9 and 12) in order to introduce the same fluid at the same pressure in order to generate the desired vortex effect within the conveyance component 10 of the valve. The fluid source 20 may be regulated with a gauge 36 to control the flow and pressure therefrom through separate transfer lines 38, 40, 42 to the injectors 12, 14, 16. Typical sizes of the diameter of the transport column of the conveyance component are 19 mm, 21 mm, 23 mm, 25 mm, 27 mm, and 29 mm. In order to achieve the desired results, the structures may be produced in the following manner, dependent, certainly, upon specific sizes of base structures as it concerns the end-use desired.

Thus, for manufacturing purposes, one manner of achieving such conveyance components of the present invention would be within the following steps:

Mechanical Prosthetic Heart Valve Unit

1. A cylindrical tube structure 10 is made titanium or titanium alloy made of sufficient diameter to connect to existing valve depending whether the prosthesis is used implantation attaching to mitral, aortal, or tricuspid heart valves. Also, the unit needs to be sufficient for either a native or artificial valve. The seamless tube structure 10 is drilled for ports (2, 4, and 6 in FIG. 1, for example) and polished. Note: The cylindrical base diameter can vary to accommodate patients of varying ages and body designs, hence valve size, chamber depth and stroke volume. Common sizes could be a range from 33 mm.-17 mm. but not limited thereto.

2. Fluid injectors 12, 14, 16 of similar material are attached to the cylinder base 10. Attachment can be accomplished in a variety of ways, but not limited to welding, flange attachment of varying types, and solid block direct bore involving taking solid block titanium and titanium allows and machining the base cylinder and the fluid injectors from one solid block of material. Flow straighteners can be inserted as desired fluid injectors of various styles; such as, but not limited to straight perpendicular, angular perpendicular, reduced leading edge, pronounced leading edge, perpendicular with directional angular inlet.

3. Calibrate and attach the fluid injectors 12, 14, 16. Note: the fluid injectors 12, 14, 16 can be of one-piece construction with the tubular cylinder 10. The ports 2, 4, 6 can be machined to improve efficiency of the unit whereas the inside diameter of the port on the interior proximal side of the cylinder 10 is as close as possible to the diameter of the fluid entrance on the distal side of the fluid injector 12, 14, 16. Precise boring can improve the efficiency of the injector up to 62%. The unit can be treated with a pyrolytic carbon coating to reduce the propensity for the patient/user to suffer from thrombosis.

4. Attach any necessary flanges 22 to the cylinder prosthesis. It is well known by those skilled in the art that a substantially conventional sewing ring is affixed by sutures (not-shown) to the living tissues (not-shown), various annular suturing members rings and suturing to the native heart tissue surrounding the existing valve.

5. Attach tethers 24, 26 lines to cylinder base 10. The attaching hardware 28, 30 can be constructed of titanium and titanium alloys due to its bio-compatible basis and reduced thrombosis affect (such titanium or one of various titanium alloys are selected with care to prevent allergic reactions, such is prevalent with, in one example, nickel-titanium a/k/a nitinol, a poor choice as a large percentage of potential patients would experience an allergic reaction).

6. The opposite eyelet 28, 30 Dacron sewing strap attachment 24, 26 can be sutured to the chamber wall or annulus for its bio-compatible features. Those skilled in the art in the light of the present disclosure that various configurations are possible within the scope of the invention, the criteria being that the attachment cooperate with the hereinafter described to distribute the surface tension to the area of attachment and to secure the valve base along its best axis of operation, such that the desired flow is directional and non-obstructive to the native and/or artificial valve it assists. The tethers 24, 26 would be anchored to the chamber wall to limit the movement of transport chamber during ejection cycle. The existing art in the field supports such anchoring system as currently utilized over the past ten years. This would define a chamber valve of a free-float design whose valve function is to alter the flow rate and thus dynamic pressure to aid native and artificial existing heart valve achieve increased throughput and thus improve cardiac output with reduced energy required from the native chamber. Dacron strap material could be utilized over a titanium alloy tie loop with a larger surface area to be sutured to the chamber wall or annulus to restrain movement during ejection cycle. Dacron would be excellent candidate for its bio-compatible properties and its aversion to thrombosis.

It will be recognized by those skilled in the art in light of the present disclosures that various configurations for the tether tie loops and attachments are possible within the scope of the present invention, the criteria being that the attachment provide camming surface to cooperate with the hereinafter described.

Other variables that would change the dynamic pressure of the prosthetic valve and hence the heart chamber is as follows:

1. The dimensional size, length, wall thickness and material the tubular and or cylindrical base is constructed of.
2. The number of orifices and the locations they are placed on the transport column.
3. Various attachment of suture rings and or suture-less attachments rings of varying designs.
4. Three dimensional modeling 3-D, and four dimensional modeling 4-D, in which three dimensional objects are tested for flow patterns in a dynamic pressure chamber for flow characteristics, as well as finite element analysis and modeling for further improving hemodynamics of inventive device.
5. The diameter of the fluid injectors, wall thickness, approach angle, leading and following edge angle, and even the material the injector is constructive of and/or treated with, such as; medical grade urethane and plastics, nylatron, nylon and various alloys.
6. Another variable that can be added is a radiographic ring such as; chromium, /or embedded micro-gps chip.
7. The shape of the cylinder can be altered to effect dynamic pressure. For example, the shape of the cylinder can be hexagonal rather than cylindrical or any irregular shape to affect the energy level from the vortex effect; this will in turn change the dynamic pressure of the valve and hence the chamber.
8. Another important note is that the vortex effect does not have to be perfectly symmetric to work.

In terms, then, of the actual operation of the invention, for all structures, basically. With a few notable exceptions, the tubular and or cylindrical transport structure is to contain the material being conveyed or transported. The ports with or without orifices are to convey blood angularly against the interior sidewall of the cylinder to create differential pressure that creates a vortex effect inside the cylinder. Calibrate and attach fluid injectors to cylinder. The size, angle, and number of fluid injectors depend on the dynamic pressure flow required by the application. For example, a 19 mm. diameter cylinder might require fewer ports than a 27 mm. cylinder and or the diameter of the fluid injectors might be three (3) mm. versus a five (5) mm. respectively. The angle of the fluid injector in relation to the cylinder wall will affect velocity.

The low-pressure area would serve as a vacuum and as the pressure would attempt to equalize more blood would exit the chamber on the positive pressure end of the tube to aid the chamber output and more blood would enter the vacuum low pressure side of the transport column. As the fluid injectors flow starts motion more blood would enter the open orifice as the pressure outside the orifice attempted to equalize based on the laws of fluid dynamics, and the cycle would continue. This would reduce the amount of energy to open the chamber valve while attributing to gains in chamber output. The valve would appear to pump itself, when, in actuality, the pressure differential of a fluid entering a restricted orifice striking angularly a cylinder wall converts the kinetic energy into a vortex effect force that reduces the frictional drag of a transport column temporarily reducing the specific weight of the material in the transport column. This leads to an increased flow rate exiting the column.

The unit is also directional and configured to increase acceleration when installed in the conveyance direction and to decrease acceleration when installed in reverse. The chamber will create negative pressure on the opposite end of the transport column as the push end of the column creates positive pressure.

Having described the invention in detail it is obvious that one skilled in the art will be able to make variations and modifications thereto without departing from the scope of the present invention. Accordingly, the scope of the present invention should be determined only by the claims appended hereto.

What is claimed is:

1. A prosthetic heart valve, comprising:
   a tubular or cylindrical frame element base having an interior surface, said frame element base being formed from a solid block of metal;
   a circular frame element opening for passage of blood through said tubular or cylindrical frame element base;
   openings present on an outer circumference of said frame element base that are perpendicularly or angularly configured thereon;
   a flow column to transport blood directionally through said frame element base;
   a plurality of fluid injectors attached to said openings present on said frame element base to perpendicularly or angularly inject fluid from outside said frame element base into said frame element base;
   wherein said plurality of fluid injectors are housed on an external portion of said frame element base;
   a plurality of flanges surrounding said circular frame element; and
   tether lines to secure said frame element base to a portion of a patient's heart.

2. A prosthetic heart valve of claim 1 wherein said frame element base is a mechanical valve.

3. The prosthetic heart valve of claim 1 wherein said frame element base includes a xenograft.

4. The prosthetic heart valve of claim 1 wherein said frame element base includes a homograft.

5. The prosthetic heart valve of claim 1 wherein said frame element base is made from titanium or an alloy thereof.

6. The prosthetic heart valve where of claim 1 wherein said frame element base is coated with a pyrolytic carbon coating.

7. The prosthetic heart valve of claim 1 wherein said fluid injectors are configured and sized radially in relation to said frame element base to create an optimal hemodynamic vortex effect thereby generating laminar flow improvement.

8. The prosthetic heart valve of claim 2 wherein said frame element base is made from titanium or an alloy thereof.

9. The prosthetic heart valve of claim 2 wherein said plurality of fluid injectors is made from titanium and any alloy thereof.

10. The prosthetic heart valve of claim 1 wherein said plurality of fluid injectors is made from titanium and any alloy thereof.

* * * * *